US006818795B2

(12) United States Patent
Perego et al.

(10) Patent No.: US 6,818,795 B2
(45) Date of Patent: Nov. 16, 2004

(54) PROCESS FOR THE PREPARATION OF MIXTURES OF METHYLENEDIANILINE AND ITS HIGHER HOMOLOGOUS PRODUCTS

(75) Inventors: Carlo Perego, Carnate (IT); Alberto De Angelis, Legnano (IT); Aldo Bosetti, Vercelli (IT)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/239,741
(22) PCT Filed: Mar. 19, 2001
(86) PCT No.: PCT/EP01/03021
§ 371 (c)(1), (2), (4) Date: Mar. 24, 2003
(87) PCT Pub. No.: WO01/74755
PCT Pub. Date: Oct. 11, 2001

(65) Prior Publication Data
US 2003/0171619 A1 Sep. 11, 2003

(30) Foreign Application Priority Data
Mar. 31, 2000  (IT) .......................................... MI00A0681

(51) Int. Cl.$^7$ ................................................ C07C 29/60
(52) U.S. Cl. ........................ 564/332; 564/331; 564/334
(58) Field of Search ................................ 564/331, 332, 564/334

(56) References Cited

U.S. PATENT DOCUMENTS 4,039,580 A  *  8/1977  Frulla et al. ................. 564/332
4,294,987 A  * 10/1981  Prather et al. ............... 564/331
5,241,119 A  *  8/1993  Clerici et al. ............... 564/332

* cited by examiner

Primary Examiner—Brian J. Davis

(57) ABSTRACT

Process for the production of methylenedianiline and its higher homologous products which comprises reacting aniline, or one of its derivatives, and formaldehyde, or one of its precursors, in one or two reactors in the presence of a solid acid catalyst selected from a zeolite or a silico-alumina, distilling off the reaction water or the water added with the reagents.

12 Claims, No Drawings

PROCESS FOR THE PREPARATION OF MIXTURES OF METHYLENEDIANILINE AND ITS HIGHER HOMOLOGOUS PRODUCTS

The present invention relates to a process for the production of mixtures or methylenedianiline (MDA) and its higher homologous products.

More specifically, the present invention relates to a process for the preparation of MDA or mixtures of MDA and its higher homologous products, wherein said mixtures contain compounds having the following general formula (I):

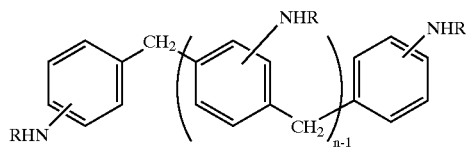

wherein R represents a hydrogen atom or a $C_1$–$C_8$ alkyl, $C_4$–$C_{10}$ cycloalkyl or $C_6$–$C_{12}$ aromatic radical and n is an integer greater than or equal to one, such as to give a functionality ranging from 2 to 6.

Methylenedianiline or mixtures of methylenedianiline are mainly used as intermediates in the preparation of the corresponding methylenediisocyanate (MDI), used in turn in the synthesis of a series of compounds such as for example polyurethanes, thermoplastic polymers and epoxy resins.

Methylenedianiline is normally produced from aniline or one of its derivatives by condensation with formaldehyde in the presence of solutions of strong acids, such as hydrochloric acid, sulfuric acid and phosphoric acid, as described, for example, in U.S. Pat. Nos.2,683,730, 3,277,173, 3,344,162, 3,362,979 or in H. Ulrich, "Chemistry and Technology of Isocyanates" John Wiley and Sons, USA, 1996. The operating conditions necessary for having a product with certain structural characteristics and without the formation of significant quantities of by-products, require the use of a large quantity of strong acid and consequently the use of materials capable of resisting these acids in the plant. Furthermore, once MDA has been synthesized, a corresponding quantity of base (typically sodium hydroxide) is necessary for neutralizing the acid used, causing the formation of large quantities of salts which must be disposed of. All these requirements cause an increase in the production costs and difficulties in running the process.

There are numerous patents which describe improvements in production processes by means of strong acid catalysts, for example by carrying out the synthesis in the presence of hydrophobic solvents in order to totally or partially recycle the acid catalyst in the aqueous phase. Processes of this type are described, for example, in U.S. Pat. Nos. 4,924,028 and 4,914,236. These improvements are not substantial and involve however the introduction of another solvent (generally chlorinated) into the process, different from the starting substrate, thus increasing risks relating to environmental impact.

Various alternative methods to this productive approach have been developed since the seventies'. U.S. Pat. Nos. 4,039,580 and 4,039,581 describe the use of re-usable solid acids, in particular clays, in the synthesis of MDA from aniline and formaldehyde. In particular, the process of U.S. Pat. No. 4,039,581 comprises pre-condensation between aniline and formaldehyde at a low temperature (molar ratio aniline/formaldehyde equal to 10), and the elimination of the water and methanol (coming from the formaldehyde which is normally available in solution at 37% in water, with methanol as stabilizer). Anilineacetals of formaldehyde (aminals) are thus obtained which are put in contact with the solid acid catalyst, at a temperature ranging from 20 to 55° C., until they are 85–100% by weight converted to the corresponding benzylamines. At this point, the temperature is brought first to a range of 55–65° C., so that 75–90% of the benzylamines are converted to end-products, then to 80–100° C. to obtain complete conversion.

U.S. Pat No. 4,071,588 describes an analogous approach by means of catalysis with solid acid catalysts of the Superfiltrol type, in which the distribution of the isomers (in particular 2,4-MDA) is modulated on the basis of the condensation operating conditions selected.

These processes however have the disadvantage that the acid catalysts described require the almost total absence of water in the anilineacetal or in its solution in solvent. This water value must not be higher than 3% by weight, preferably lower than 0.15% by weight, in order to avoid deactivation of the catalyst. Clays, moreover, also have problems as they can be re-used for a limited number of times and, due to their natural and non-synthetic nature, with not completely reproducible performances depending on the specific lots.

Other solid compounds used for catalyzing the synthesis of MDA are various oxides. For example, patents WO 98/37124 and U.S. Pat. Nos. 4,284,816 and 4,287,364 describe the preparation of MDA using oxides of elements of groups IV–VI of the periodic table (for example titanium, zirconium and molybdenum), or borides and sulfides of tungsten or inter-metallic molybdenum-aluminum compounds. Although these catalysts in some cases improve the yields and productivity of the clays, they cause the formation of non-marginal quantities of various kinds of by-products.

The Applicant has now found a new process, for the production of compounds having general formula (I), starting from aniline, or its derivatives, and formaldehyde, or a compound capable of giving formaldehyde, in the presence of regenerable solid acid catalysts, such as for example zeolites, or zeolite-similar materials, and amorphous silico-aluminas. These catalysts, consisting of zeolites with medium and large pores characterized by a spaciousness index ranging from 2.5 to 19 in acid form, partially or totally exchanged, such as beta zeolite, mordenite, ZSM-12, etc. or amorphous silico-aluminas with a varying content of aluminum characterized by a pore diameter ranging from 20 to 500 Å, are capable of catalyzing the synthesis of MDA or the mixture of methylenedianiline having general formula (I) with a high activity and selectivity to the compounds of interest. They are also capable of providing a good catalytic activity in the presence of quantities of water of even 1% approx. by weight. Furthermore, as they are of a synthetic nature, they have an excellent performance reproducibility.

Further advantages of the present process include the high yield of methylenedianiline (MDA) without the use of corrosive acid reagents and the possibility, in the production of isocyanates with phosgene starting from the above mixtures, of effecting a closed chlorine cycle in the industrial site. This lowers the risk of environmental impact on the part of the productive site.

An object of the present invention therefore relates to a process for the production of compounds having general formula (I) which comprises:

(a) reacting aniline or one of its derivatives, and formaldehyde, or one of its precursors, in proportions ranging from 2 to 10 moles of aniline per mole of formaldehyde, at a temperature ranging from 10–60° C. and in the absence of an acid catalyst, so as to form an aminal mixture in aniline (the aniline is generally used in great excess with respect to the formaldehyde);

(b) separating the water from the aminal mixture to a residual concentration of water equal to about 1–2% by weight;

(c) optionally diluting the solution previously formed in step (b), in aniline;

(d) isomerizing the aminal mixture by feeding it into one or more fixed bed reactors containing a solid acid catalyst selected from a zeolite or a silico-alumina, at a temperature ranging from 100 to 250° C., preferably from 150 to 210° C., and at atmospheric pressure or at a value which is such as to maintain the reagent mixture in the liquid state;

(e) removing the aniline from the methylenedianiline, or its higher homologous products, using known purification techniques such as distillation, for example.

According to the present invention, the reagents of step (a) can be fed batchwise, in continuous or semi-continuous, starting from aniline and formaldehyde (or their derivatives or precursors). The precondensate is subsequently fed to a fixed bed reactor containing the solid acid catalyst, after removal of the water.

In order to favour the subsequent separation and recycling, the feeding of the aminal precondensate can be partialized by operating with a vertical reactor equipped with two or more lateral inlets.

The separation of the water from the aminal mixture is effected according to the conventional techniques such as decanting or distillation. The latter can be carried out at temperatures and pressures which vary according to the degree of residual water to be obtained in the aminal solution. The separation of the water can also be effected using a combination of the known techniques, such as for example, decanting followed by distillation.

The aminal mixture is isomerized in the presence of a zeolitic acid catalyst. Examples of catalysts are zeolites in acid form having a spaciousness index ranging from 2.5 to 19, extremes included, such as beta zeolite, mordenite, ZSM-12, MCM-22 and ERB-1. The beta zeolite described in U.S. Pat. No. 3,308,069 with a spaciousness index of 19, is preferred.

Further examples of acid catalysts are silico-aluminas amorphous to X-rays, with a molar ratio $SiO_2/Al_2O_3$ ranging from 10/1 to 500/1, a porosity ranging from 0.3 to 0.6 ml/g and a pore diameter ranging from 20 to 500 Å. The preferred silico-alumina is MSA described in U.S. Pat. No. 5,049,536.

At the end of the re-arrangement reaction of the aminal mixture, the composition of the mixture obtained after isomerization can be further modified in the distribution of its components, by totally or partially recycling the mixture itself to the aminal synthesis zone or to the isomerization reactor.

A further object of the present invention relates to a process for the production of compounds having general formula (I) which comprises reacting aniline, or one of its derivatives, and formaldehyde, or one of its precursors, in a single reactor with complete mixing in the presence of a solid acid catalyst selected from a zeolite or a silico-alumina, as described above, continuously distilling the reaction water or the water added with the reagents.

The single-step process is based on the use of slurry reactors, both stirred and bubbled. The reagents, aniline (or one of its derivatives) and formaldehyde (or one of its precursors) together with the solid acid catalyst, are con- temporaneously fed to the slurry reactor. The feeding can be effected either continuously or by partializing the addition of one or more components of the reaction mixture, over a period of time.

The molar ratios aniline/formaldehyde used vary from 0.5 to 10, preferably from 2.2 to 5. The reaction temperature ranges from 30 to 230° C., preferably from 120 to 200° C., whereas the pressure has a value which is such that the water added with the reagents or formed during the reaction, is continuously removed by means of a suitable distillation system connected to the reactor. The residence times in the liquid phase range from 0.5 to 10 hours and more preferably from 1 to 8 hours.

When the catalyst is changed, it can be completely changed over a time ranging from a minimum of 5 hours to a maximum of 30 hours. The weight ratio catalyst/charge ranges from 1/20 to 1/300.

The catalyst used is preformed so that it can be used under the desired operating conditions. The slurry reactor can therefore be charged with the catalyst in microspheres, which can be prepared with spray-dryer techniques as described, for example, in European patent 265,018 or in Italian patent 1,295,267, or with sol-gel techniques as described in European patent 791,558.

At the end of the reaction, after filtration of the catalyst, the mixture is sent to a removal section of the excess aniline (and possible residual water) from the desired product, using conventional techniques such as distillation.

The mixture of methylenedianiline synthesized according to the procedures described above, can be transformed into the corresponding mixture of isocyanates by means of the known techniques.

Some illustrative but non-limiting examples are provided for a better understanding of the present invention and for its embodiment.

EXAMPLE 1—TWO-STEP PROCESS

Synthesis of the Intermediate

The intermediate (precondensate or aminal) having the general formula:

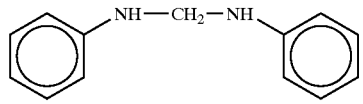

together with its higher homologous products, is prepared by condensation between aniline and formaldehyde. In particular, an aqueous solution at 37% of formaldehyde is added, under stirring, to a reaction container containing aniline, so as to have a molar ratio aniline/formaldehyde equal to four. The temperature is brought to 45° C. and maintained as such for the whole reaction.

At the end of the addition, the mixture is maintained under stirring for an hour, the aqueous phase is then separated from the organic phase consisting of the aminal and non-reacted excess aniline. The organic phase is then dried to a water content of 1.25% and conserved for the subsequent tests. The drying is effected by stirring the organic phase for 30 minutes with anhydrous sodium sulfate and subsequent filtration.

EXAMPLE 2—TWO-STEP PROCESS

Catalytic Test 5 ml of extruded beta zeolite, prepared according to the procedure described in Examples 3 and 4 of Italian patent application MI99A001171, are charged into a tubular reactor having a diameter of 12.5 mm and a length of 390 mm. The extruded beta zeolite, with a ligand content equal to 50%, is ground and sieved to 70÷100 mesh. The aminal mixture obtained in Example 1, diluted at 70% by volume in aniline, is then fed to the reactor at a temperature of 180° C., a pressure of 4 bars and an LHSV (Liquid Hourly Space Velocity) of 1 $h^{-1}$ referring to the active phase.

Samples are then taken at the times indicated in Table 1, which, after removal of the reduced aniline pressure (solvent), are analyzed by means of HPLC, with the analysis method described in the Journal für Praktische Chemie, Band 328, Heft 1, 1986, pages 142–148.

TABLE 1

| Time (h) | Conversion (%) | 4.4'MDA (%) | 2,4'MDA (%) | Trimers (%) | Heavy products (%) |
|---|---|---|---|---|---|
| 4 | 97.6 | 51.58 | 30.41 | 13.67 | 1.94 |
| 20 | 99.9 | 37.69 | 32.20 | 23.72 | 4.76 |
| 26 | 99.9 | 40.89 | 27.51 | 27.44 | 4.16 |
| 48 | 99.9 | 41.17 | 29.23 | 22.44 | 4.09 |
| 56 | 99.9 | 41.14 | 26.48 | 28.14 | 4.24 |
| 72 | 99.9 | 41.26 | 25.94 | 28.02 | 4.78 |
| 96 | 99.9 | 44.94 | 26.7 | 26.13 | 2.23 |
| 106 | 99.9 | 44.15 | 25.42 | 26.26 | 4.17 |
| 140 | 99.9 | 49.11 | 26.91 | 18.91 | 5.07 |
| 166 | 99.9 | 48.83 | 25.26 | 23.78 | 2.13 |
| 190 | 99.9 | 46.91 | 24.21 | 24.26 | 4.62 |
| 210 | 99.9 | 46.79 | 22.73 | 25.47 | 5.01 |
| 230 | 99.9 | 47.65 | 16.37 | 28.04 | 3.04 |
| 240 | 99.9 | 50.53 | 22.79 | 21.02 | 5.66 |

The table indicates under heavy products, the higher homologous products of MDA with a molecular weight of over 300.

EXAMPLE 3—SINGLE-STEP PROCESS

Catalytic Test 4 g of beta zeolite in powder form (with a particle size distribution of 0.1–0.6 microns) and 53.5 g of aniline are charged into a 250 ml glass reactor, equipped with a magnetic stirrer, drip funnel and Claisen distiller. The stirred suspension is then heated to 150° C. and 3.52 g of a solution of formaldehyde at 37% are added dropwise to the suspension over a period of 30 minutes. During the addition, both the water in the solution of formaldehyde and that formed during the reaction, are distilled at the head.

At the end of the addition (considered as time =0), the suspension is continually stirred and maintained at 150° C. A sample is taken after 2 hours and is analyzed, after removing the aniline, via HPLC with the method indicated in Example 2. The results are provided in Table 2.

TABLE 2

| Time (h) | Conversion (%) | 4.4'MDA (%) | 2,4'MDA (%) | Trimers (%) | Heavy products (%) |
|---|---|---|---|---|---|
| 0 | 99.9 | 52.16 | 33.0 | 13.23 | 1.61 |
| 2 | 99.9 | 54.21 | 34.82 | 8.34 | 2.63 |

EXAMPLE 4—SINGLE-STEP PROCES (Catalytic Test)

1 g of beta zeolite in powder form (with a particle size distribution of 0.1–0.6 microns) and 53.5 g of aniline are charged into a 250 ml glass reactor, equipped with a magnetic stirrer, drip funnel and Claisen distiller. The stirred suspension is then heated to 150° C. and 3.52 g of a solution of formaldehyde at 37% are added dropwise to the suspension over a period of 30 minutes. During the addition both the water in the solution of formaldehyde and that formed during the reaction, are distilled at the head.

At the end of the addition (considered as time=0), the suspension is continually stirred and maintained at 150° C. A sample is taken after 2, 4 and 6 hours, which is analyzed, after removing the aniline, via HPLC with the method indicated in Example 2. The results are provided in Table 3.

TABLE 3

| Time (h) | Conversion (%) | 4.4'MDA (%) | 2,4'MDA (%) | Trimers (%) | Heavy products (%) |
|---|---|---|---|---|---|
| 0 | 93.61 | 10.74 | 6.78 | 41.57 | 34.52 |
| 2 | 99.9 | 52.34 | 35.25 | 9.60 | 2.81 |
| 4 | 99.9 | 55.59 | 36.51 | 6.71 | 1.19 |
| 6 | 99.9 | 55.72 | 34.47 | 6.46 | 0.84 |

EXAMPLE 5—SINGLE-STEP PROCESS

With the Partialized Addition of Formaldehyde 4 g of beta zeolite in powder form (with a particle size distribution of 0.1–0.6 microns) together with 53.5 g of aniline are charged into a 250 ml glass reactor, equipped with a magnetic stirrer, drip funnel and Claisen distiller. The stirred suspension is then heated to 150° C. and 14.08 g of a solution of formaldehyde at 37% are added dropwise to the suspension over a period of 60 minutes. During the addition both the water in the solution of formaldehyde and that formed during the reaction, are distilled at the head. At the end of the addition, a sample is removed, which is analyzed with the usual methods (sample 1).

A further quantity of 7.04 g of a solution of formaldehyde at 37% is then added with the same method, over a period of 60 minutes. At the end of the addition, another sample is taken, which is analyzed with the usual methods (sample 2).

The additions of formaldehyde (7.04 g each time) are repeated a third (sample 3) and fourth (sample 4) time. The total time of the test is therefore 4 hours.

The results are listed in Table 4. It can be seen that the repeated addition of formaldehyde gives an end-mixture of products having a composition richer in trimers and heavy products with respect to the results of Examples 3 and 4.

TABLE 4

| Time (h) | Conversion (%) | Molar ratio aniline/CH$_2$O | 4.4'MDA (%) | 2,4'MDA (%) | Trimers (%) | Heavy products (%) |
|---|---|---|---|---|---|---|
| 1 | 99.9 | 3.12 | 33.54 | 17.27 | 40.49 | 8.70 |
| 2 | 99.9 | 2.04 | 31.61 | 13.69 | 36.31 | 18.39 |
| 3 | 99.5 | 1.55 | 15.68 | 7.89 | 39.87 | 35.25 |
| 4 | 99.5 | 1.24 | 8.41 | 4.33 | 31.72 | 55.16 |

What is claimed is:

1. A process for the production of compounds having general formula (I)

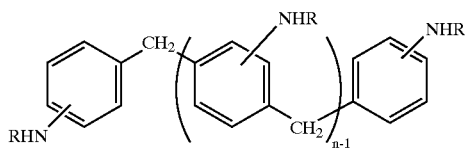

wherein R represents a hydrogen atom or a $C_1$–$C_8$ alkyl, $C_4$–$C_{10}$ cycloalkyl or $C_6$–$C_{12}$ aromatic radical an n is an integer greater than or equal to one, such as to give a functionality ranging from 2 to 6, which comprises:

reacting aniline or one of its derivatives represented by the formula

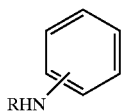

wherein R is as previously defined, and formaldehyde, or a compound capable of producing formaldehyde, in proportions ranging from 2 to 10 moles of aniline per mole of formaldehyde, at a temperature ranging from 10–60° C. and in the absence of an acid catalyst, so as to form an aminal mixture in aniline;

(b) separating the water from the aminal mixture to a residual concentration of water equal to about 1–2% by weight;

(c) optionally diluting the solution previously formed in step (b), in aniline;

(d) isomerizing the aminal mixture by feeding it into one or more fixed bed reactors containing a solid acid catalyst selected from a zeolite or a silico-alumina, at a temperature ranging from 100 to 250° C., and at atmospheric pressure or at a value which is such as to maintain the reagent mixture in the liquid state;

(e) removing the aniline from the methylenedianiline, or its higher homologous products, by means of distillation.

2. The process according to claim 1, wherein the reagents in step (a) are fed batchwise, in continuous or semi-continuous.

3. The process according to claim 1 or 2, wherein the feeding of the aniline, or one of its derivatives, is fed stepwise, operating with a vertical reactor equipped with two or more lateral inlets.

4. The process according to claim 1, wherein the solid acid catalyst is selected from zeolites in acid form having a spaciousness index ranging from 2.5 to 19.

5. The process according to claim 4 wherein the solid acid catalyst is selected from silico-aluminas amorphous to X-rays, with a molar ratio $SiO_2/Al_2O_3$ ranging from 10/1 to 500/1, a porosity ranging from 0.3 to 0.6 ml/g and a pore diameter ranging from 20 to 500 Å.

6. The process according to claim 1, wherein the composition of the mixture obtained after isomerization is modified in the distribution of its components by totally or partially recycling the mixture itself to the aminal synthesis zone or to the isomerization reactor.

7. A process for the production of compounds having general formula (I)

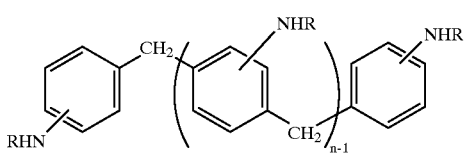

wherein R represents a hydrogen atom or a $C_1$–$C_8$ alkyl, $C_4$–$C_{10}$ cycloalkyl or $C_6$–$C_{12}$ aromatic radical an n is an integer greater than or equal to one, such as to give a functionality ranging from 2 to 6, which comprises reacting aniline, or one of its derivatives represented by the formula

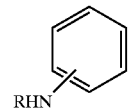

wherein R is as previously defined, and formaldehyde, or a compound capable of producing formaldehyde in a single reactor with complete mixing in the presence of a solid acid catalyst selected from a zeolite or a silico-alumina, and continuously distilling off the reaction water or the water added with the reagents.

8. The process according to claim 7, wherein both the reagents and the solid acid catalyst are fed either continuously or by stepwise addition of one or more components of the reaction mixture over a period of time.

9. The process according to claims 7 or 8, wherein the reaction mixture is discharged from the reactor either in continuous or batchwise.

10. The process according to any of the claims from 7 or 8, wherein the molar ratios between aniline and formaldehyde range from 0.5 to 10.

11. The process according to any of the claims from 7 or 8, wherein the reaction temperature ranges from 30 to 200° C.

12. The process according to claim 7 wherein the weight ratio charge/catalyst ranges from 1/20 to 1/300.

* * * * *